(12) United States Patent
Stadler et al.

(10) Patent No.: US 8,639,333 B2
(45) Date of Patent: Jan. 28, 2014

(54) METHOD AND APPARATUS FOR ADAPTIVE CARDIAC RESYNCHRONIZATION THERAPY EMPLOYING A MULTIPOLAR LEFT VENTRICULAR LEAD

(75) Inventors: Robert W. Stadler, Shoreview, MN (US); Aleksandre T. Sambelashvili, Maple Grove, MN (US); Vincent E. Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 95 days.

(21) Appl. No.: 13/301,012

(22) Filed: Nov. 21, 2011

(65) Prior Publication Data

US 2013/0131750 A1   May 23, 2013

(51) Int. Cl.
*A61N 1/365* (2006.01)
(52) U.S. Cl.
USPC ............................................... 607/25
(58) Field of Classification Search
USPC ................................... 607/17, 25
See application file for complete search history.

(56) References Cited

U.S. PATENT DOCUMENTS

| | | | |
|---|---|---|---|
| 5,683,432 A | 11/1997 | Goedeke | |
| 6,418,346 B1 | 7/2002 | Nelson | |
| 6,442,433 B1 | 8/2002 | Linberg | |
| 6,599,250 B2 | 7/2003 | Webb | |
| 6,622,045 B2 | 9/2003 | Snell | |
| 7,181,284 B2 | 2/2007 | Burnes | |
| 7,254,442 B2 | 8/2007 | van Gelder | |
| 7,555,336 B2 | 6/2009 | Sheth | |
| 7,697,985 B2 | 4/2010 | Kaiser | |
| 7,706,879 B2 | 4/2010 | Burnes | |
| 7,787,951 B1 | 8/2010 | Min | |
| 7,848,807 B2 | 12/2010 | Wang | |
| 2003/0083709 A1* | 5/2003 | Zhu et al. | 607/27 |
| 2005/0149138 A1 | 7/2005 | Min | |
| 2008/0294218 A1 | 11/2008 | Savage | |
| 2009/0043351 A1 | 2/2009 | Sathaye | |
| 2009/0054942 A1 | 2/2009 | Zhu | |
| 2010/0042174 A1 | 2/2010 | Koh et al. | |
| 2011/0022110 A1 | 1/2011 | Min | |
| 2011/0022112 A1 | 1/2011 | Min | |
| 2011/0098770 A1 | 4/2011 | Ryu et al. | |

FOREIGN PATENT DOCUMENTS

| | | |
|---|---|---|
| WO | 02/051496 A2 | 7/2002 |
| WO | 2005/063333 A1 | 7/2005 |
| WO | 2010/039501 A1 | 4/2010 |

OTHER PUBLICATIONS (PCT/US2012/064029) PCT Notification of Transmittal of the International Search Report and the Written Opinion of the International Searching Authority.

* cited by examiner

*Primary Examiner* — Eric D. Bertram
(74) *Attorney, Agent, or Firm* — Michael C. Soldner (57) ABSTRACT

A medical device and associated method control the delivery of a cardiac pacing therapy by selecting first and second pacing sites along a first ventricle of a patient's heart and delivering the pacing therapy by pacing the first ventricle using the first pacing site during the periods of a first ventricular pacing mode and using the second pacing site during periods of a second ventricular pacing mode. In one embodiment, the device determines activation times at multiple sites along a ventricle in response to pacing pulses being delivered to the opposite ventricle. A first pacing site is selected in response to the activation time determination. The device delivers the pacing therapy by pacing the first ventricle using the first pacing site during periods of the first ventricular pacing mode.

9 Claims, 4 Drawing Sheets

METHOD AND APPARATUS FOR ADAPTIVE CARDIAC RESYNCHRONIZATION THERAPY EMPLOYING A MULTIPOLAR LEFT VENTRICULAR LEAD

FIELD OF THE DISCLOSURE

The disclosure relates generally to medical devices and, in particular, to a medical device and associated method for controlling cardiac resynchronization therapy.

BACKGROUND

Cardiac resynchronization therapy (CRT) is a treatment for heart failure patients in which one or more heart chambers are electrically stimulated (paced) to restore or improve heart chamber synchrony. Achieving a positive clinical benefit from CRT is dependent on the location of the pacing site, particularly in the left ventricle (LV). Thus, placement of the pacing leads, especially an LV pacing lead is important in promoting a positive outcome from CRT. As multi-polar cardiac pacing leads become commercially available, multiple pacing electrode vectors are possible, for example, for pacing in the LV. A need remains for selecting which pacing electrode vector(s) are used for delivering CRT in a most efficacious way.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In "adaptive CRT", pacing pulses may be delivered in both the right and left ventricle (biventricular pacing) or only in the left ventricle (LV-only pacing or single ventricle pacing). The pacing device is configured to switch between biventricular pacing and single ventricle LV-only pacing based on measurements of atrial-to-ventricular (AV) conduction. However, an LV pacing vector selected for biventricular pacing may not necessarily be the optimal LV pacing vector for LV-only pacing. A system and associated method for controlling LV pacing vector selection during adaptive CRT is described herein for providing optimal CRT benefit during both biventricular and LV-only pacing modes. During either biventricular or single ventricle LV-only pacing, the atrial chambers may or may not be paced. For descriptions of methods and devices that may be implemented for delivering adaptive CRT, reference is made to U.S. Pat. No. 7,254,442 (van Gelder et al.), U.S. Pat. No. 7,181,284 (Burnes, et al.), and U.S. Pat. No. 7,706,879 (Burnes, et al.), hereby incorporated herein by reference in their entirety.

The present disclosure relates to a medical device and associated method to control the delivery of a cardiac pacing therapy by selecting first and second pacing sites along a first ventricle of a patient's heart and delivering the pacing therapy by pacing the first ventricle using the first pacing site during periods of a first ventricular pacing mode and using the second pacing site during periods of a second ventricular pacing mode. In one embodiment, the device measures activation times at multiple sites along a first ventricle in response to pacing pulses being delivered to the opposite ventricle. A first pacing site is selected in response to the activation time measurements. The device delivers the pacing therapy by pacing the first ventricle using the first pacing site during periods of biventricular pacing.

For example, techniques for selecting a left ventricular pacing site used for delivering single-ventricle pacing in the left ventricle and for selecting a left ventricular pacing site used for delivering biventricular pacing are described. In one embodiment, adaptive CRT is delivered and includes periods of single ventricle pacing in the left ventricle with no pacing in the right ventricle and periods of biventricular pacing. Single ventricle pacing in the left ventricle is delivered using the selected left ventricular pacing site for single ventricle pacing and biventricular pacing is delivered using the selected pacing site in the left ventricle for biventricular pacing.

Figure 1:
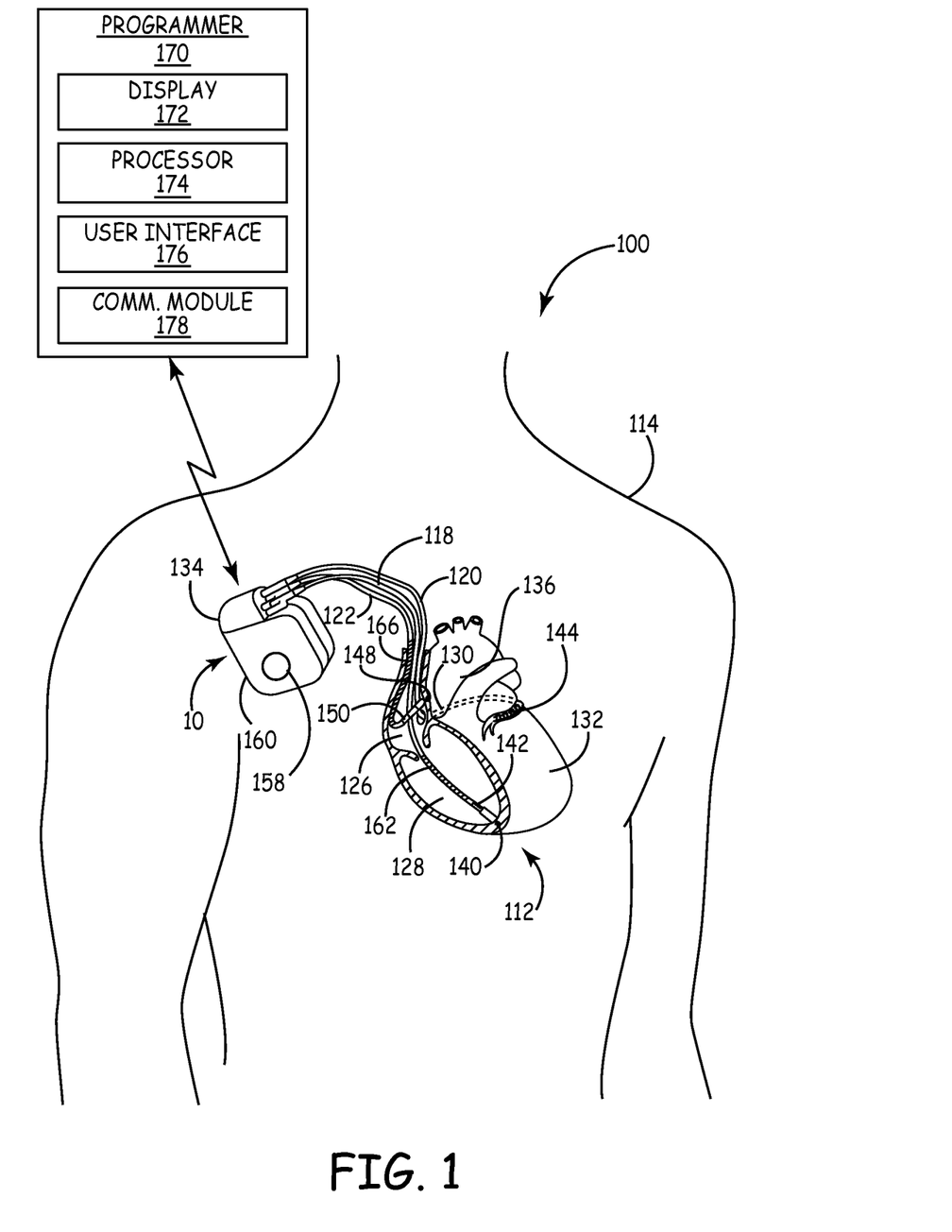
FIG. 1 is a schematic diagram of one embodiment of an implantable medical device (IMD) system in which techniques disclosed herein may be implemented to provide therapy to a patient's heart.

FIG. 1 is a schematic diagram of one embodiment of an IMD system 100 in which techniques disclosed herein may be implemented to provide therapy to heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122. IMD 10 is capable of delivering at least biventricular and LV-only pacing, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect arrhythmias of heart 112, such as fibrillation of ventricles 128 and 132, and deliver defibrillation therapy to heart 112 in the form of electrical pulses. While IMD 10 is shown in a right pectoral implant position in FIG. 1, a more typical implant position, particular when IMD 10 is embodied as an ICD, is a left pectoral implant position.

IMD 10 includes internal circuitry for performing the functions attributed to IMD 10, and a housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT therapy, which includes the use of a selected pacing vector for LV pacing that utilizes at least one electrode 144 on multipolar LV lead 120. IMD 10 is configured to pace in one or both ventricles 128 and 132 for controlling and improving ventricular synchrony. The methods described herein may be implemented in a dual or multi-chamber pacemaker or ICD delivering pacing pulses to the right and left ventricles using programmable pacing pulse timing parameters and programmable pacing vectors. In particular, IMD 10 is configured to provide "adaptive CRT" which automatically switches between biventricular pacing and LV-only pacing in response to changes in the patient's AV conduction. When AV conduction is impaired or blocked, or more generally when AV conduction time is slowed, biventricular pacing is delivered. When normal AV conduction returns, LV-only pacing is delivered. In this way, RV pacing is delivered only when needed based on the patient's own AV conduction status, which may fluctuate over time.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological or diagnostic information from IMD 10. A user may also interact with programmer 170 to program IMD 10, e.g., select values for operating parameters of the IMD. A user interacting with programmer 170 may request IMD 10 to perform a pacing site optimization algorithm and transmit results to programmer 170 or request data stored by IMD 10 relating to pacing site analysis procedures performed automatically by IMD 10 on a periodic basis.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, MICS, or as described in U.S. Pat. No. 5,683,432 "Adaptive Performance-Optimizing Communication System for Communicating with an Implantable Medical Device" (Goedeke, et al). In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote management of a patient using the techniques described herein. Remote patient management systems may be configured to utilize the presently disclosed techniques to enable a clinician to review cardiac signal data and authorize programming of IMD pace control parameters. Reference is made to commonly-assigned U.S. Pat. Nos. 6,599,250 (Webb et al.), 6,442,433 (Linberg et al.), 6,418,346 (Nelson et al.), and 6,480,745 (Nelson et al.) for general descriptions and examples of network communication systems for use with implantable medical devices for remote patient monitoring and device programming.

Figure 2:
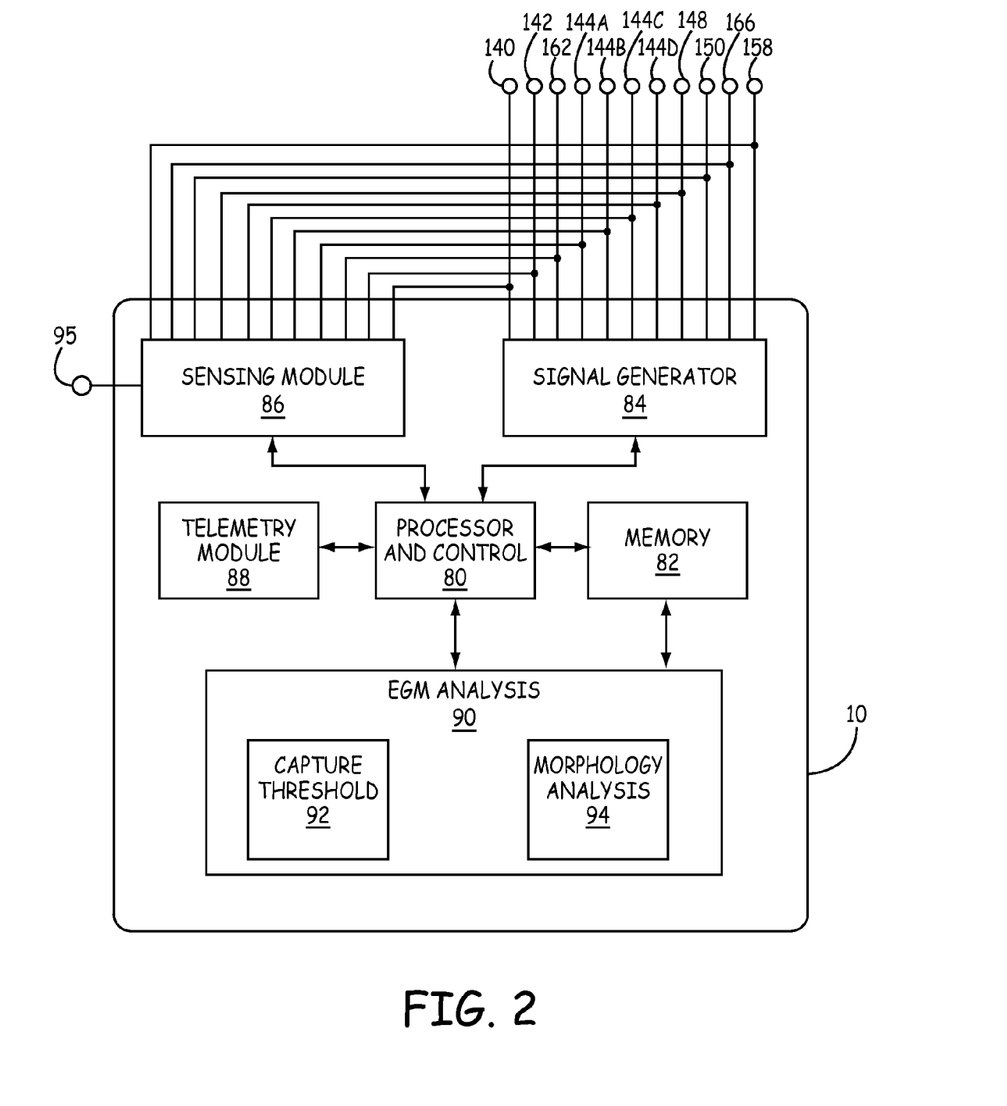
FIG. 2 is a block diagram illustrating one example configuration of the IMD shown in FIG. 1.

FIG. 2 is a block diagram illustrating one example configuration of IMD 10. In the example illustrated by FIG. 2, IMD 10 includes a processor and control unit 80, memory 82, signal generator 84, sensing module 86, and telemetry module 88. IMD 10 further includes EGM signal analysis module 90, which itself may include a capture threshold detection module 92 and an EGM morphology analysis module 94.

Memory 82 may include computer-readable instructions that, when executed by processor 80, cause IMD 10 and processor 80 to perform various functions attributed throughout this disclosure to IMD 10, processor 80, sensing module 86, and EGM analysis module 90. The computer-readable instructions may be encoded within memory 82. Memory 82 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, EGM analysis module 90 may, at least in part, be stored or encoded as instructions in memory 82 that are executed by processor and control 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. Signal generator 84 is configured to deliver cardiac pacing pulses, which are delivered according to atrial-ventricular (AV) and/or inter-ventricular (VV) timing intervals for delivering CRT.

Signal generator 84 may include a switch module (not shown) and processor and control 80 may use the switch module to select, e.g., via a data/address bus, which of the available electrodes are used to deliver pacing pulses. Processor 80 controls which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors signals from at least one of electrodes 140, 142, 144A-144D, 148, 150, 158, 162, or 166 in order to monitor electrical activity of heart 12. Sensing module 86 may also include a switch module to select which of the available electrodes are used to sense the cardiac activity. In some examples, processor 80 selects the electrodes to function as sense electrodes, or the sensing vector, via the switch module within sensing module 86.

Sensing module 86 includes multiple detection channels, each of which may be selectively coupled to respective combinations of electrodes 140, 142, 144A-144D, 148, 150, 158, 162, or 166 to detect electrical activity of a particular chamber of heart 112. Each detection channel may comprise an amplifier that outputs an indication to processor 80 in response to sensing of a cardiac depolarization, in the respective chamber of heart 112. In this manner, processor 80 may detect the occurrence of R-waves and P-waves in the various chambers of heart 112. The occurrence of R-waves sensed using a local bipolar sensing electrode pair is used in measuring relative activation times at different candidate pacing sites for use in selecting a pacing site. Sensing of R-waves or other features of a QRS signal attendant to the depolarization of the myocardial tissue along a sensing electrode site at each of electrodes 144 is used to identify a pacing site associated with a relatively late activation of the LV.

The occurrence of R-waves in the RV is used in monitoring AV conduction time. In particular, prolongation of the AV conduction time or the detection of AV block based on R-wave sensing during no ventricular pacing (or pacing at an extended AV interval that allows intrinsic conduction to take place) is used to control adaptive CRT.

Sensing module 86 may further include digital signal processing circuitry for providing EGM analysis module 90 with digitized EGM signals. Alternatively, analog EGM signals may be provided to EGM analysis module 90 and digitized as needed for performing EGM signal analysis.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event, e.g., in another chamber.

EGM analysis module 90 may provide additional EGM signal analysis capabilities using signals from sensing module 86. The capture threshold module 92 may be included to detect capture and/or loss of capture (LOC) when signal generator 84 delivers a pacing pulse. Capture threshold information may be used with other EGM analysis information for selecting pacing sites. EGM morphology analysis may be used in some embodiments for verifying capture or determining optimal pacing control parameters. For example, a VV interval used during biventricular pacing may be determined based on a QRS signal width measured from an EGM signal. Determination of relative LV local activation times at the sites of electrodes 144 may utilize digital EGM signal analysis performed by module 90.

It is further contemplated that methods described herein may be implemented using other physiological signals for determining optimal pacing parameters for delivering CRT.

In some embodiments, another type of physiological sensor 95 other than cardiac electrodes is coupled to sensing module 86 and used for obtaining a signal correlated to the hemodynamic or mechanical function of the heart. Sensor 95 may be embodied as a mechanical, optical or other type of transducer, such as a pressure sensor, oxygen sensor, accelerometer, or any other sensor that is responsive to cardiac function and produces a signal corresponding to cardiac mechanical function. Analysis of the signal may be used in guiding selection of AV and VV intervals used to control CRT pacing pulses.

Figure 3:
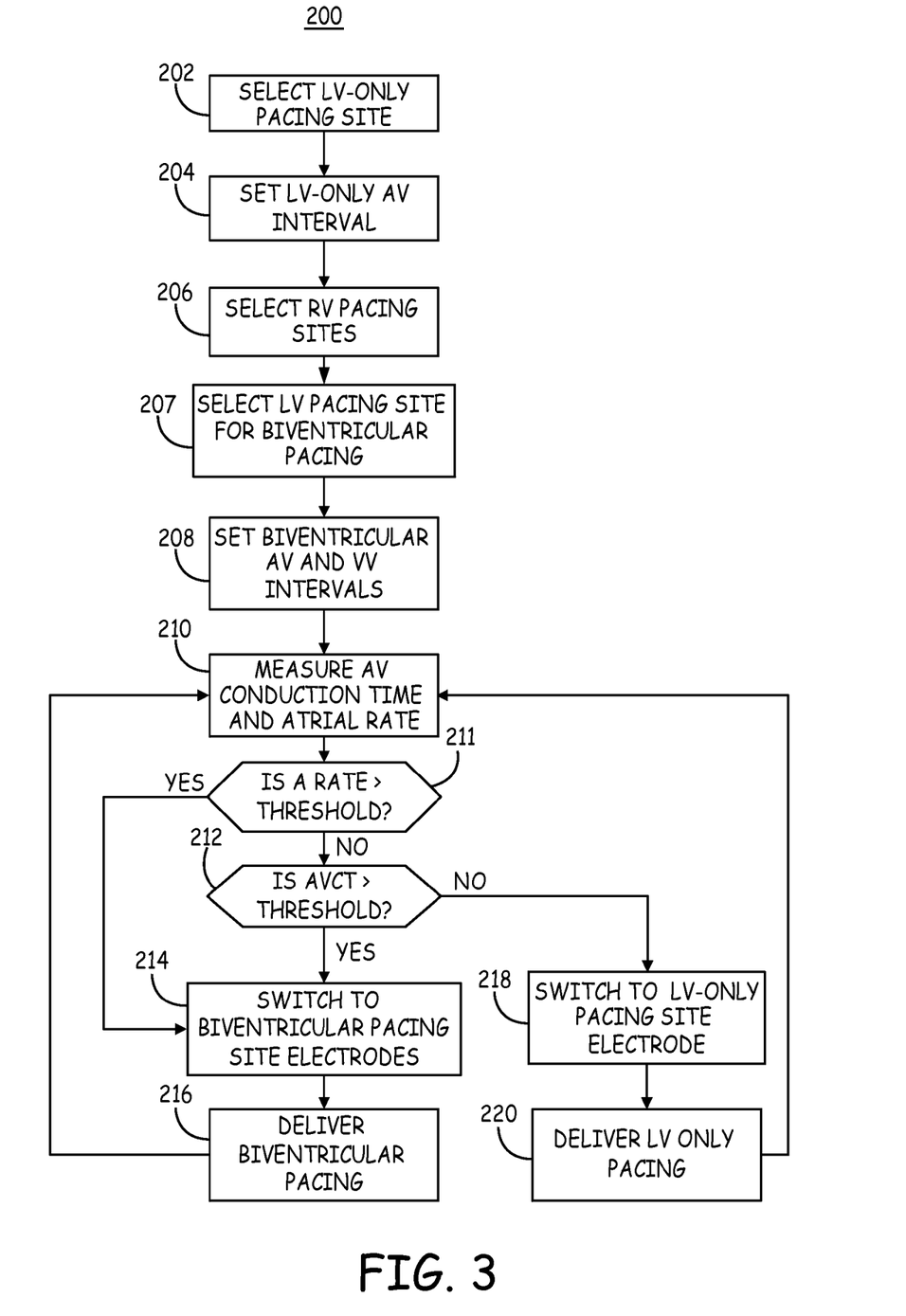
FIG. 3 is a flow chart of a method for controlling pacing electrode selection during a cardiac pacing therapy according to one embodiment.

FIG. 3 is a flow chart 200 of a method for controlling pacing electrode selection during a cardiac pacing therapy according to one embodiment. Flow chart 200 and other flow charts presented herein are intended to illustrate the functional operation of the device, and should not be construed as reflective of a specific form of software or hardware necessary to practice the methods described. It is believed that the particular form of software, firmware, hardware or combination thereof will be determined primarily by the particular system architecture employed in the device and by the particular signal sensing and therapy delivery methodologies employed by the device. Providing software, firmware, and/or hardware to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a pacing site is selected along the LV for delivering LV-only pacing during adaptive CRT. The LV-only pacing site may be selected according to established criteria or clinician preference. In one embodiment, the LV-only pacing site is selected as a site of late electrical activation during intrinsic ventricular conduction. In CRT, the greatest therapeutic benefit may be achieved when the LV is paced at or near a location associated with late intrinsic activation time of the ventricle. An LV activation time is the time interval measured from a reference time point to a sensed R-wave at an LV pace/sense electrode site. The reference time point may be an atrial sensed or paced event, an R-wave sensed in the RV, or another fiducial point identified on a QRS complex sensed from an acquired EGM signal. In one embodiment, the LV activation times are measured by sensing for an LV depolarization wavefront (R-wave) at each of the LV electrodes 144 used as sensing electrodes.

A late electrical activation time is an activation time that occurs relatively later than activation (myocardial depolarization) at other possible LV pace/sense electrode locations. A late activation time is not necessarily the latest LV activation time that can be measured in the LV since prolonged activation may be associated with pathological or diseased tissue such as myocardial scar tissue, which would be undesirable as a pacing site.

In other embodiments, the LV-only pacing site may be selected using other measurements or techniques, which may or may not be combined with measuring LV activation times. For example, hemodynamic measurements may be performed to determine which pacing site results in the greatest hemodynamic benefit. Hemodynamic measurements may be obtained from other physiological sensors 95 coupled to IMD 10 or using clinical techniques such as Doppler echocardiography, fluoroscopy, or LV catheterization.

While the illustrative embodiments presented herein refer to selecting a single LV pacing site for LV-only pacing, it is recognized that with the availability of multi-polar leads positioned along the LV, one or more sites may be selected. For example, one or more intravenous, endocardial or epicardial leads may be placed for LV pacing and one or more pacing sites may be identified for improving ventricular synchrony during LV-only pacing. As such, when an LV pacing site is selected at block 202, this selection may include two or more pacing sites along the LV.

The operation of selecting a pacing site at block 202 and at other pacing site selection blocks described herein may include performing measurements, e.g., for determining a site of relatively late electrical activation in the LV, automatically or upon user command, and automatically programming a pacing site based on those measurements. In other embodiments, selecting a pacing site may include performing measurements automatically or upon command and then transmitting the measurements to an external programmer 170 to present the results and/or a recommended pacing site based on the measurements to a physician. The physician may then accept the recommended site or program a different site using this information and program the IMD accordingly.

At block 204, an AV interval for controlling the LV-only pacing is set. The AV interval is set relative to an intrinsic AV conduction time measured between the atria and the RV in one embodiment. For example, during no ventricular pacing, the time interval between an atrial sensed P-wave or atrial pacing pulse and a subsequent R-wave sensed in the RV is measured. The sensed R-wave may be determined from a bipolar or unipolar RV sensing electrode vector. In other embodiments, the AV conduction time is measured between a paced or sensed atrial event and a fiducial point on a QRS complex obtained from an RV EGM signal. The LV-only pacing AV interval can be set a predetermined interval less than the measured AV conduction time or a percentage thereof to enable earlier activation of the LV relative to the RV to restore or improve ventricular synchrony. This method of measuring the AV conduction time and setting an LV-only pacing AV interval for controlling the timing of LV pacing pulses (relative to a sensed or paced atrial event) may be performed automatically by the IMD and repeated periodically or upon request to update the AV interval setting.

In other embodiments, the AV interval may be initially established using clinical methods, such as echo Doppler, fluoroscopy, LV catheterization or other techniques. In still other embodiments the AV interval may be set based on other sensor signals or measurements obtained automatically by the IMD that provide an indication of the hemodynamic or mechanical function of the heart.

At blocks 206 through 208, parameters for controlling biventricular pacing are determined. At block 206, an RV pacing site is selected. A RV pacing site may be a nominal or default pacing site, for example RV apical pacing using RV tip electrode 140 and RV ring electrode 142. At block 207, an LV pacing site for use during biventricular pacing is selected. The LV pacing site during biventricular pacing that yields the greatest improvement in ventricular synchrony may be distinct from the LV pacing site used during LV-only pacing. As such, an algorithm for selecting the LV pacing site during LV-only pacing and an algorithm for selecting the LV pacing site during biventricular pacing are performed to separately determine the optimal LV pacing site for the two modes of ventricular pacing. The result may be the same LV pacing site for both LV-only and biventricular pacing or different LV pacing sites. As mentioned previously, when an LV pacing site is selected, this selection may include two or more pacing sites along the LV. As such, for both LV-only pacing and for biventricular pacing, a LV pacing site selection may include selecting one or more pacing sites along the LV for pacing the LV.

In one embodiment, the LV pacing site for biventricular pacing is selected by measuring LV activation times during RV pacing. At block 207, LV activation time intervals are measured from an RV pacing pulse to sensed R-waves or a fiducial point on QRS signals obtained from EGM signals measured at each of the available LV electrodes 144. An LV electrode measuring a late activation time is selected as the LV pacing site during biventricular pacing. The LV electrode selected may correspond to the site at which the latest LV activation time is measured following an RV pacing pulse. As discussed above, however, sometimes the latest LV activation time is associated with myocardial scar or ischemic tissue making the site undesirable as a pacing site.

As such, additional operations may be performed at blocks 204 and 207 for verifying that the site of latest activation is not associated with myocardial scar or local ischemia. Detection for the evidence of scar tissue or ischemia could include measurement of a high pacing capture threshold at the electrode site by capture threshold module 92, observation of delayed exit of a pacing-induced evoked response from the pacing site (i.e., delayed initiation of QRS complex from the pacing pulse), or by observation of a small QRS complex or fractionated QRS complex in the EGM obtained using a short sensing bipole including the candidate pacing site electrode and determined by EGM analysis module 90. A small or fractionated QRS complex would be identified from the EGM signal obtained using the electrode at the pacing site when pacing is not delivered at that site, i.e., either during intrinsic rhythm or possibly during pacing at a distant site.

A high capture threshold, delayed exit of the evoked response QRS, or altered QRS complex during sensing at the latest activation site as evidence of scar or ischemic tissue would result in a rejection of the latest activation site as a pacing site. If other pacing sites are still available, the electrode site having the next latest activation time may be selected. This site may also be evaluated for any pathological abnormalities that would indicate an undesirable pacing site.

After identifying an LV pacing site associated with late electrical activation, AV and VV intervals for controlling the timing of biventricular pacing pulses are set at block 208. The AV interval is used for controlling the delivery of RV pacing pulses following a sensed or paced atrial event. Generally, this interval is set to be shorter than an intrinsic AV conduction time such that the pacing pulse is delivered in the RV before an intrinsically conducted depolarization reaches the RV from the atrium. In one embodiment, the AV interval is set a predetermined interval longer than the end of a P-wave signal obtained from an EGM signal. For example the AV interval may be set to extend approximately 30 to 40 ms after the end of a P-wave signal. The AV interval may be verified as being at least a predetermined interval shorter than an intrinsic AV conduction time or calculated as a linear function of the intrinsic AV conduction time. For example, the AV interval may be required to at least 50 ms (or another interval) shorter than the measured intrinsic AV conduction time. Practice of the methods described herein for selecting and controlling an LV pacing site during adaptive CRT is not necessarily limited to any particular criteria or techniques for setting an AV interval for controlling the timing of an RV pacing pulse during biventricular pacing and clinicians may use preferred methods for setting the AV interval, VV intervals or other pacing control parameters.

The VV interval controlling the timing between an RV pacing pulse and an LV pacing pulse during biventricular pacing is also set at block 208. The VV interval is set based on measurements of the intrinsic AV conduction time and intrinsic QRS duration during no ventricular pacing in one embodiment. The intrinsic AV conduction time may be measured as described previously, between an atrial paced or sensed event and an RV R-wave or QRS complex fiducial point during no ventricular pacing. The intrinsic QRS width is measured from a unipolar or far-field signal so as to obtain a relatively global signal of the ventricular depolarization as opposed to a more locally sensed QRS signal obtained from a ventricular bipolar electrode vector. In an alternative embodiment, the VV interval is set based upon the RV to LV conduction time as measured from the local electrograms.

If the intrinsic AV conduction time is long, e.g. greater than a predetermined threshold, and the QRS signal is wide, based on a previously established QRS width threshold, the VV interval may be set to zero or the RV may be paced a short interval earlier than the LV. If the AV conduction time is short and the QRS is narrow, the LV is paced first and the RV is paced second. According to one convention, a positive VV interval causes the LV to be paced earlier than the RV and a negative VV interval causes the RV to be paced earlier than the LV. It is contemplated that other methods for selecting an optimal VV interval may be used for restoring ventricular synchrony during biventricular pacing, including methods that rely on measuring a physiological signal correlated to the hemodynamic or mechanical function of the heart or using clinical methods such as echocardiography, fluoroscopy, or heart catheterization.

At block 210, atrial P-waves attendant to the depolarization of the atrial chamber are sensed to enable measurement of time intervals associated with atrial depolarizations. An atrial rate may be determined by measuring P-P intervals for detecting fast atrial rates, atrial tachycardia or atrial fibrillation. Additionally or alternatively, the AV conduction time is measured as an interval between a sensed P-wave and subsequent R-wave sensed from a ventricular EGM signal. The measured atrial rate may be used in combination with the measured AV conduction time are used in controlling switching between biventricular and LV-only pacing modes.

AV conduction time can be measured by withholding ventricular pacing or extending the AV pacing interval for one or more cardiac cycles to allow intrinsic activation of the ventricles to be sensed. When ventricular pacing is withheld, a safety pacing pulse may be scheduled to prevent asystole. An AV conduction time is measured as the time interval from an atrial sensed P-wave or paced event to a sensed R-wave in the RV, for example. If complete AV block is present, a safety pacing pulse may be delivered (or pacing at a maximum AV interval) indicating the intrinsic AV conduction time is greater than the safety pacing pulse time interval or maximum AV conduction time. During some AV conduction time measurements, a far-field EGM signal is also recorded by the IMD and analyzed to automatically measure and update the durations of the P-wave and QRS complex for use in updating the AV interval and VV interval.

It is recognized that some patients may present sustained or intermittent episodes of atrial or ventricular tachycardia. In the case of atrial or ventricular tachycardia, the ventricular pacing mode is switched to biventricular pacing. AV conduction time will not be measured during periods of tachycardia. If an atrial tachycardia is detected, including atrial fibrillation or atrial flutter, and causes a pacing mode switch the ventricles will be paced in a biventricular pacing mode at a ventricular pacing rate that is independent of the intrinsic atrial rhythm. This pacing mode switch may be made in response to detecting an atrial tachycardia by measuring P-P intervals at block 211. At block 214, the biventricular pacing site electrodes are coupled to the signal generator, and biventricular pacing is delivered using the selected pacing sites at block 216.

When AV conduction time (AVCT) is measured at block 210 and the atrial rate is regular (block 211), the AVCT is compared, at decision block 212, to criteria for determining whether the IMD will operate in a biventricular pacing mode or an LV-only pacing mode for delivering CRT. In one embodiment, if the AVCT is greater than a previously established threshold, the IMD will deliver biventricular pacing. If the AVCT is less than the threshold, AV conduction is intact and the IMD will deliver LV-only pacing to allow the natural conduction system of the heart to set the atrial-ventricular rhythm. The ventricular synchrony is improved by delivering LV pacing at the selected LV-only pacing site.

In response to an AVCT exceeding a threshold at block 212, switching circuitry is controlled to connect the selected LV-only pacing site electrode(s) to the signal generator at block 218 for delivering LV pacing pulses at block 220. The LV-only pacing pulses are delivered at the AV interval set at block 204. The AVCT is periodically checked at block 210. As long as the AVCT remains within the threshold for LV-only pacing, as determined at decision block 212, LV-only pacing is maintained using the selected LV-only pacing site.

If the AVCT is found to exceed the threshold at decision block 212, the switching circuitry in signal generator 84 is controlled to couple the RV and the LV electrodes selected for biventricular pacing to the signal generator for delivering biventricular pacing. Biventricular pacing is delivered at block 216 using the AV and VV intervals set for biventricular pacing at block 208. In some embodiments, an additional requirement for LV-only pacing may include an intrinsic heart rate less than a predetermined threshold (block 211). In such embodiments, both the intrinsic AV conduction time and the intrinsic heart rate must be below predetermined thresholds to enable LV-only pacing and otherwise biventricular pacing is enabled.

It is recognized that different criteria may be established for controlling switching between biventricular and LV-only pacing in various embodiments. For example, the AVCT may be required to meet a threshold requirement for more than one cardiac cycle before switching between biventricular and LV-only pacing. In one illustrative embodiment, if one long AVCT is measured that exceeds a threshold, e.g. approximately 200 ms, the IMD controller may switch from LV-only pacing to biventricular pacing. During biventricular pacing, AVCT is periodically measured and at least three consecutive AVCTs less than the threshold are required to cause the IMD controller to switch from biventricular pacing back to LV-only pacing.

In another example, hysteresis may be applied in defining AVCT thresholds. For example, the AVCT threshold set for switching from LV-only pacing to biventricular pacing may be a higher threshold than an AVCT threshold set for switching from biventricular pacing to LV-only pacing. In this way, a somewhat longer AVCT is required (for one or more cardiac cycles) to initiate biventricular pacing and a relatively shorter AVCT (for one or more cardiac cycles) will cause LV-only pacing to be initiated.

Furthermore, criteria other than AVCT may be used for determining when the ventricular pacing mode is switched between biventricular and LV-only pacing. As mentioned previously, the presence of atrial tachycardia will cause the ventricular pacing mode to be switched to biventricular pacing. In some embodiments, a maximum atrial rate may be set above which ventricular pacing no longer tracks the atrial rate. For example, if the atrial rate exceeds some threshold rate during LV-only pacing, the ventricular pacing mode may switch to a biventricular pacing mode.

Regardless of the criteria being used to cause the switching between biventricular and LV-only pacing, each time the switch is made, the controller causes switching circuitry included in the signal generator 84 to couple the appropriate electrodes selected for LV-only pacing or the electrodes selected for biventricular pacing.

Figure 4:
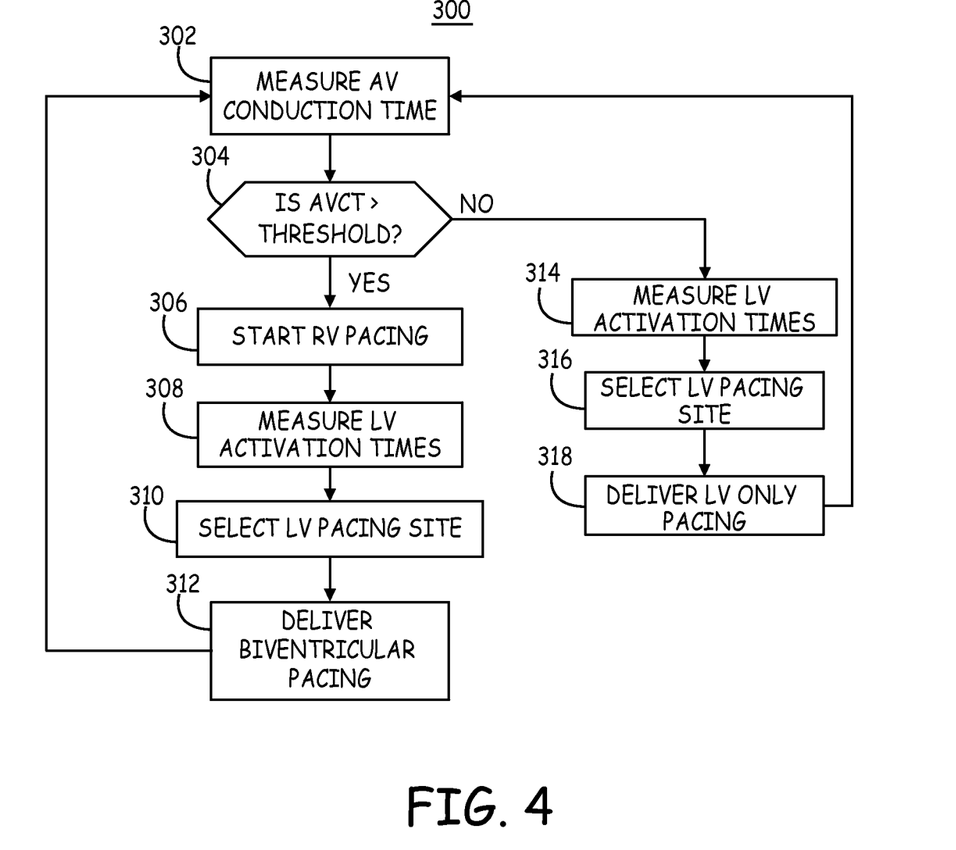
FIG. 4 is a flow chart of a method for controlling adaptive CRT according to an alternative embodiment.

FIG. 4 is a flow chart 300 of an alternative embodiment for controlling adaptive CRT. During CRT delivery, the AVCT is measured at block 302 on a periodic basis, e.g., by temporarily extending the AV pacing interval or withholding ventricular pacing, to detect a change in AV conduction. Prolongation of AVCT indicates a worsening of AV conduction and a probable need for biventricular pacing. A return to normal AVCT indicates restoration of AV conduction. Intrinsic RV conduction is desirable over RV apical pacing when AV conduction is intact. Restoration of AV conduction is an indication for LV-only pacing.

If the AVCT exceeds a threshold (or an atrial rate as described previously) at block 304, RV pacing is initiated at block 306. During one or more RV paced cycles, an electrical activation time is measured at block 308 corresponding to each available LV electrode site, e.g. at electrodes 144 in FIG. 1. An LV electrode corresponding to a site of late activation is selected as the LV pacing site at block 310, and biventricular pacing is delivered at block 312 using the selected LV electrode and previously selected RV electrodes used during the RV pacing at block 306. LV bipolar or unipolar pacing may be delivered using the selected LV pacing site electrode(s).

The AVCT continues to be monitored periodically at block 302 during biventricular pacing. If the AVCT is found to fall below the threshold at block 304 for a required number of cardiac cycles during a conduction test, intrinsic AV conduction is restored. Only LV pacing is required to improve ventricular synchrony. As discussed previously, the AVCT threshold criteria applied during biventricular pacing for triggering a switch to LV-only pacing may be set differently than the AVCT threshold criteria applied during LV-only pacing for triggering a switch to biventricular pacing.

In one example embodiment, in response to measuring an AVCT that is less than the threshold at block 304, LV activation times are measured at block 314, during no ventricular pacing for one or more cardiac cycles. LV activation times are measured by sensing for R-waves in the LV during atrial sensing or pacing using all available LV electrodes. An electrode site associated with a late activation time is selected as the LV pacing site at block 316. LV-only pacing is delivered at block 318 using the selected LV pacing site.

An AV interval for use during LV-only pacing and AV and VV intervals used during biventricular pacing may be previously determined according to methods described above. As such, each time the pacing mode switches between biventricular and LV-only pacing in response AVCT measurements, an optimal LV pacing site is selected upon switching pacing modes that corresponds to a late activation time during intrinsic ventricular conduction (for LV-only pacing) or during RV pacing (for biventricular pacing). It is recognized that sometimes the LV pacing sites selected for LV-only and for biventricular pacing may be the same sites. Other times the selected LV pacing sites may be different for the two different ventricular pacing modes. By determining a site of late activation separately during intrinsic ventricular conduction and during RV pacing, an optimized LV pacing site can be selected for each pacing mode, i.e. biventricular and single ventricle LV-only pacing, to promote the greatest benefit of adaptive CRT in restoring ventricular synchrony during periods of biventricular pacing and during periods of LV-only pacing.

In another variation of the embodiment shown in FIG. 4, the LV activation times may not be measured every time the ventricular pacing mode is switched. Rather, the LV activation times may be measured every $i^{th}$ time or after a predetermined time interval has elapsed so that the selected LV pacing sites for biventricular and LV-only pacing are updated periodically.

Thus, a medical device and associated methods for controlling and delivering a pacing therapy have been presented in the foregoing description with reference to specific embodiments. It is appreciated that various modifications to the referenced embodiments may be made without departing from the scope of the disclosure as set forth in the following claims.

The invention claimed is:

1. A medical device for controlling and delivering a cardiac therapy, the device comprising:
a plurality of electrodes positioned along a first ventricle and a second ventricle of a patient's heart;
a signal generator coupled to the plurality of electrodes to deliver pacing pulses to the first ventricle and the second ventricle via the plurality of electrodes;
a sensing module coupled to the plurality of electrodes to sense cardiac signals; and
a controller coupled to the signal generator and the sensing module and configured to:
select a first pacing site along the first ventricle of a patient's heart from the plurality of electrodes;
select a second pacing site along the first ventricle from the plurality of electrodes;
control the signal generator to deliver a pacing therapy comprising periods of a first ventricular pacing mode and periods of a second ventricular pacing mode by pacing the first ventricle at the first pacing site during the periods of the first ventricular pacing mode and at the second pacing site during the periods of the second ventricular pacing mode;
determine a first activation time at each of a plurality of sites along the first ventricle in response to pacing pulses being delivered to a second ventricle; and
select the first pacing site in response to the determined first activation times.

2. The device of claim 1, wherein the first ventricular pacing mode is a biventricular pacing mode and the second ventricular pacing mode is a single ventricle pacing mode.

3. The device of claim 2, wherein the controller is further configured to set a first atrial-ventricular interval and an interventricular interval to control biventricular pacing pulses and set a second atrial-ventricular interval to control single ventricle pacing pulses.

4. The device of claim 1, wherein the controller is further configured to:
receive sensed atrial signals associated with atrial depolarizations from the sensing module;
determine time intervals associated with the sensed atrial signals; and
switch between the first ventricular pacing mode and the second ventricular pacing mode in response to the determined time intervals.

5. The device of claim 1, wherein the controller is further configured to:
- determine an atrioventricular conduction time;
- compare the atrioventricular conduction time to a threshold; and
- control the signal generator to deliver pacing pulses to the second ventricle and to determine the first activation times in response to the atrioventricular conduction time exceeding the threshold.

6. The device of claim 1, wherein one of selecting the first pacing site and selecting the second pacing site comprises selecting a plurality of pacing sites along the first heart chamber.

7. A medical device for controlling and delivering a cardiac therapy, the device comprising:
- a plurality of electrodes positioned along a first ventricle and a second ventricle of a patient's heart;
- a signal generator coupled to the plurality of electrodes to deliver pacing pulses to the first ventricle and the second ventricle via the plurality of electrodes;
- a sensing module coupled to the plurality of electrodes to sense cardiac signals; and
- a controller coupled to the signal generator and the sensing module and configured to:
  - select a first pacing site along the first ventricle of a patient's heart from the plurality of electrodes;
  - select a second pacing site along the first ventricle from the plurality of electrodes;
  - control the signal generator to deliver a pacing therapy comprising periods of a first ventricular pacing mode and periods of a second ventricular pacing mode by pacing the first ventricle at the first pacing site during the periods of the first ventricular pacing mode and at the second pacing site during the periods of the second ventricular pacing mode;
  - determine a second activation time at each of the plurality of sites along the first ventricle in response to no pacing pulses being delivered to the second ventricle; and
  - select the second pacing site in response to the determined second activation times.

8. The device of claim 7, wherein the controller is further configured to:
- determine an atrioventricular conduction time;
- compare the atrioventricular conduction time to a threshold; and
- determine the second activation times in response to the atrioventricular conduction time being less than the threshold.

9. A medical device for controlling and delivering a cardiac therapy, the device comprising:
- a plurality of electrodes positioned along a first ventricle and a second ventricle of a patient's heart;
- a signal generator coupled to the plurality of electrodes to deliver pacing pulses to the first ventricle and the second ventricle via the plurality of electrodes;
- a sensing module coupled to the plurality of electrodes to sense cardiac signals; and
- a controller coupled to the signal generator and the sensing module and configured to:
  - select a first pacing site along the first ventricle of a patient's heart from the plurality of electrodes;
  - select a second pacing site along the first ventricle from the plurality of electrodes;
  - control the signal generator to deliver a pacing therapy comprising periods of a first ventricular pacing mode and periods of a second ventricular pacing mode by pacing the first ventricle at the first pacing site during the periods of the first ventricular pacing mode and at the second pacing site during the periods of the second ventricular pacing mode;
  - determine a first activation time at each of a plurality of sites along the first ventricle in response to pacing pulses being delivered to a second ventricle;
  - select the first pacing site in response to the determined first activation times;
  - determine a second activation time at each of the plurality of sites along the first ventricle in response to no pacing pulses being delivered to the second ventricle;
  - select the second pacing site in response to the determined second activation times; and
  - select the first pacing site and the second pacing site as sites associated with respective first and second activation times that are longer than another of the determined first activation times and second activation times, respectively.

* * * * *